US005367082A

United States Patent [19]
Bergfeld et al.

[11] Patent Number: 5,367,082
[45] Date of Patent: Nov. 22, 1994

[54] PROCESS FOR THE PREPARATION OF 2-MERCAPTOBENZOTHIAZOLE

[75] Inventors: Manfred J. Bergfeld, Erlenbach-Mechenhard; Norbert Gutlein, Oberhofen; Klaus Wohlfahrt, Elsenfeld; Eberhard Aust, Grossostheim, all of Germany

[73] Assignee: Akzo N.V., Arnhem, Netherlands

[21] Appl. No.: 11,767

[22] Filed: Feb. 1, 1993

Related U.S. Application Data

[63] Continuation-in-part of Ser. No. 755,151, Sep. 5, 1991, abandoned.

[30] Foreign Application Priority Data

Sep. 7, 1990 [DE] Germany ............... 4028473

[51] Int. Cl.$^5$ ........................... C07D 277/72
[52] U.S. Cl. ..................... 548/175; 548/176; 548/177
[58] Field of Search .............. 548/175, 176, 177

[56] References Cited

U.S. PATENT DOCUMENTS

| | | | |
|---|---|---|---|
| 1,604,199 | 10/1926 | Sebrell | 548/175 |
| 1,631,871 | 6/1927 | Kelly | 548/175 |
| 2,090,233 | 8/1937 | Roberts | 548/175 |
| 2,247,894 | 7/1941 | Smith | 548/176 |
| 3,031,073 | 4/1962 | Szlatinay | 548/175 |
| 3,770,759 | 11/1973 | Scherhag et al. | 548/176 |
| 3,975,394 | 8/1976 | Mina et al. | 260/306 |
| 4,061,646 | 12/1977 | Kawaoka et al. | 548/177 |
| 4,780,540 | 10/1988 | Denecker et al. | 548/176 |
| 5,276,206 | 1/1994 | Sicheneder et al. | 548/152 |

FOREIGN PATENT DOCUMENTS

| | | |
|---|---|---|
| 0015802A1 | 9/1980 | European Pat. Off. |
| 0015802B1 | 5/1984 | European Pat. Off. |
| 0169107A1 | 1/1986 | European Pat. Off. |
| 0169107B1 | 9/1987 | European Pat. Off. |
| 2565977A1 | 12/1985 | France |
| 1919420 | 10/1970 | Germany |
| 1941379 | 2/1971 | Germany |
| 2121394 | 11/1972 | Germany |
| 2258484 | 11/1972 | Germany |
| 2454277A1 | 11/1974 | Germany |
| 2652394A1 | 11/1976 | Germany |
| 2709989A1 | 3/1977 | Germany |
| 2816407A1 | 10/1979 | Germany |
| 2816503A1 | 10/1979 | Germany |
| 3113298 | 10/1982 | Germany |
| 3325724A1 | 7/1983 | Germany |
| 387738 | 2/1933 | United Kingdom |

OTHER PUBLICATIONS

Chemical Abstracts, *Mathematical Model of a Tubular Reactor for the Synthesis of Vulcanization Accelerators,* vol. 101, (1984) p. 63, ref. No. 153265u; Bodrov, et al.
Chemical Abstracts, *Continuous Preparation of 2-Mercaptobenzothiazole,* vol. 97, (1982) p. 828, ref. No. 182405u; Kacani, et al.
Patent Abstracts, *Production of High Purity 2–Mercaptobenzothiazole,* Shinnittetsu Kagaku et al., JP 60–25980 (A), Jun. 13, 1985, C–286, vol. 9/No. 138.
Chemical Abstracts, *Highly Pure 2–Mercaptobenzothiazole* vol. 104, 1986, p. 548, ref. No. 34057h.

*Primary Examiner*—Joseph Paul Brust
*Assistant Examiner*—MarySusan H. Gabilan
*Attorney, Agent, or Firm*—Oliff & Berridge

[57] ABSTRACT

In a process for the preparation of 2-mercaptobenzothiazole from aniline, sulfur and carbon disulfide under pressure and for separation of the 2-mercaptobenzothiazole from the crude reaction product by cooling and recycling the desirable intermediates and by-products into the reactor together with aniline, sulfur and carbon disulfide, the reaction is carried out using a residence time in the reactor of at least one hour to a time before the 2-mercaptobenzothiazole product thus-formed begins to decompose into undesirable intermediate products. A maximum hydrogen sulfide pressure is maintained on quenching to a temperature ranging between 220 and 280° C. by mixing the crude reaction product with carbon disulfide at a temperature sufficient to obtain a homogeneous quenched mixture. The hydrogen sulfide is removed completely only after crystallization of the 2-mercaptobenzothiazole.

34 Claims, 4 Drawing Sheets

PROCESS FOR THE PREPARATION OF 2-MERCAPTOBENZOTHIAZOLE

This application is a continuation-in-part of application Ser. No. 07/755,151, filed Sep. 5, 1991, abandoned.

BACKGROUND OF THE INVENTION

The present invention relates to a process for the preparation of 2-mercaptobenzothiazole from aniline, carbon disulfide and sulfur.

2-Mercaptobenzothiazole (MBT) is a starting material which is industrially very important for the preparation of vulcanization accelerators such as, for example, dibenzothiazolyl disulfide and sulphenamides.

Industrially, MBT is generally produced by the Kelly process (U.S. Pat. No. 1,631,871), wherein aniline, carbon disulfide and sulfur are reacted under elevated pressure at elevated temperatures. The resulting crude MBT must then be purified to remove unreacted starting compounds, intermediates and products from secondary reactions. The MBT purification, which is customary industrially, in principle consists of a reprecipitation, in which the crude MBT is dissolved in sodium hydroxide solution and the tar-like by-products are decanted off, filtered off or extracted. The aqueous sodium MBT solution is subjected to a further oxidative treatment, if appropriate; the MBT is then precipitated using sulfuric acid and filtered off (cf. German Patent 2,258,484).

The disadvantages of a purification of this type are that the aqueous phase contains about 85 kg of $Na_2SO_4$ per 100 kg of MBT formed, which has to be disposed of with the effluent. In addition, about 15 kg of waste products (tars) are produced per 100 kg of MBT and the bulk of these waste products has to be disposed of as solid waste, for example by means of combustion. A considerable proportion of the by-products also passes into the effluent, where it causes a high chemical oxygen demand. The chemical oxygen demand (COD) is determined in mg/l $O_2$ by back-titration of dichromate. The analytical methods vary and must be indicated by the result.

In addition, in the case of modern catalytic oxidation processes using oxygen to form MBTS and sulfenamides (compare German Pat. No. 3,113,298 and, respectively, German Pat. No. 3,325,724) a high purity of the MBT is required because it is then possible to work with very low catalyst concentrations. Such purity is not guaranteed with conventional production methods for MBT.

Those skilled in the art have therefore made many attempts to prepare MBT both in high purity and in high yield. U.S. Pat. No. 3,031,073 describes another process for the preparation of MBT, in which aniline, carbon disulfide and sulfur are heated under pressure in a cyclic procedure, the pressure is reduced, the MBT is removed from the crude product, the residue is mixed with the necessary amount of aniline, carbon disulfide and sulfur and this mixture is again heated to form MBT. Any method is said to be suitable for isolation of MBT from the crude reaction product. This patent specification points out in detail a purification method using a water/carbon disulfide emulsion, which incidentally also contains a surface-active substance.

However, according to Example 1 of the said U.S. Pat. No. 3,031,073, it is also possible to use carbon disulfide on its own as a purifying agent. After a reaction time of 5 hours at 245° C., the reaction is discontinued by releasing the pressure and removing the reaction mixture from the autoclave. With this procedure the pressure generated by hydrogen sulfide is eliminated by lowering the pressure to atmospheric pressure. In order to purify the crude product, the latter is mixed with carbon disulfide in an autoclave and the mixture is heated to 140° C. and kept at this temperature for 30 to 45 minutes. Finally, based on the purification method, MBT is obtained in a yield of 94% and in a purity which is indicated as 99.5%. When this procedure was repeated, a total yield of 82% was obtained. The MBT had a purity of 98%.

DE-OS (German Published Application) 2,652,394 describes a process for the purification of crude MBT using carbon disulfide. According to Example 1, aniline, carbon disulfide and sulfur are allowed to react for 50 minutes at 220° C. and the hydrogen sulfide is then removed. For purification, the liquid MBT is brought into contact with cold carbon disulfide, with the formation of two phases, a slurry of MBT and carbon disulfide being formed. The MBT is said to have a purity of 99.5%, which merely in view of the quoted melting range of 172° to 175° C. (literature value for pure MBT: 180°-182° C.) appears dubious. The yield was about 20% and is thus entirely uneconomical.

The purity of the MBT has an effect during the conversion to the said vulcanization accelerators. Experiments in this regard give the following findings: in oxidation reactions in accordance with German Patent No. 3,113,298 and German Patent No. 3,325,724 (preparation of MBTS and respectively, CBS or TBBS), MBT prepared and purified in accordance with U.S. Pat. No. 3,031,073 and obtained after three process cycles led to dark greasy deposits on the stirrer shaft and reactor wall. These deposits bound the catalyst and severely retarded the reaction.

There was therefore a need for an economic process for the preparation of a highly pure MBT in high yield. The recycling of intermediate and by-products should not have an adverse effect on the quality of the MBT such that oily deposits are formed in the oxidation reaction to give dibenzothiazolyl disulfide or sulfenamides and the reaction is substantially slowed down, which is reflected in a low space-time yield.

SUMMARY OF THE INVENTION

Therefore, an object of the invention is to provide a process which solves the problems mentioned.

The process according to the invention is characterized in that the reaction is carried out with a residence time in the reactor of at least 1 hour at temperatures of 220°-280° C. and said reaction is discontinued before the reaction equilibrium is reached. The residence time therefore ranges from at least one hour to a time before the thus-formed 2-mercaptobenzothiazole products begin to decompose into undesirable, irreversible by-products. Preferably, the residence time is a time after all the aniline in the reactor has reacted. A maximum hydrogen sulfide pressure at elevated temperature is maintained during quenching of a hot crude reaction product by mixing with carbon disulfide to obtain a homogeneous quenched mixture preferentially at a temperature ranging between about 80° C. and 200° C. (without releasing pressure from the hydrogen sulfide). Preferably, prior to quenching with carbon disulfide, the crude reaction product is allowed to cool to 220° C. Prior to removing hydrogen sulfide from the reactor, the quenched reaction product is further cooled to a temperature from between about 20° C. and about 70° C. The hydrogen sulfide is removed completely only after crystallization of the 2-mercaptobenzothiazole. After crystallization of 2-mercaptobenzothiazole and removal of the hydrogen sulfide, the 2-mercaptobenzothiazole is isolated.

DETAILED DESCRIPTION OF PREFERRED EMBODIMENTS

Preferably, the maximum residence time $t_{max}$, as a function of the reaction temperature $T_R$ (°K.), is given by the formula $$t_{max} = 278.3 - 101 \cdot \log T_R \text{ hours.}$$

From the formula, a maximum residence time of 6.3 hours is calculated for a reaction temperature of 220° C., a maximum residence time of 3.7 hours for a reaction temperature of 250° C. and a maximum residence time of 1.3 hours for a reaction temperature of 280° C.

Residence time is understood to be a time the reaction mixture is kept at the reaction temperature. The reaction is discontinued before the reaction equilibrium is reached and accordingly when conversion is incomplete. Preferably the reaction is discontinued very rapidly by mixing the reaction mixture with carbon disulfide, the hydrogen sulfide present in the reaction mixture not yet being removed. The reaction is at equilibrium when the concentration of MBT remains constant and the thus-formed MBT begins to decompose into undesirable intermediate reaction products.

The maintenance of a maximum hydrogen sulfide pressure up to the time of crystallization and the residence time limited as a function of the reaction temperature result in a mixture of intermediate and by-products which, on recycling, without adjustment of the composition of the feed mixture, after a certain number of return cycles, remains constant with respect to the products and their proportions. The maximum residence time should not be exceeded because otherwise the composition of the intermediates and by-products can change in such a way that they can no longer be converted to MBT, as a result of which the recycling into the process is impaired.

An exemplary reaction mechanism yielding a major product may be:

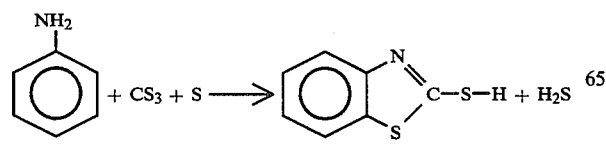

This reaction is only an indication of a starting material and a reaction product. In fact, the reaction mechanism is by far more complicated and involves the formation of intermediate products, by-products and undesirable, irreversible by-products. The present invention is likely not limited to this reaction. Indeed, exemplary desirable by-products include:

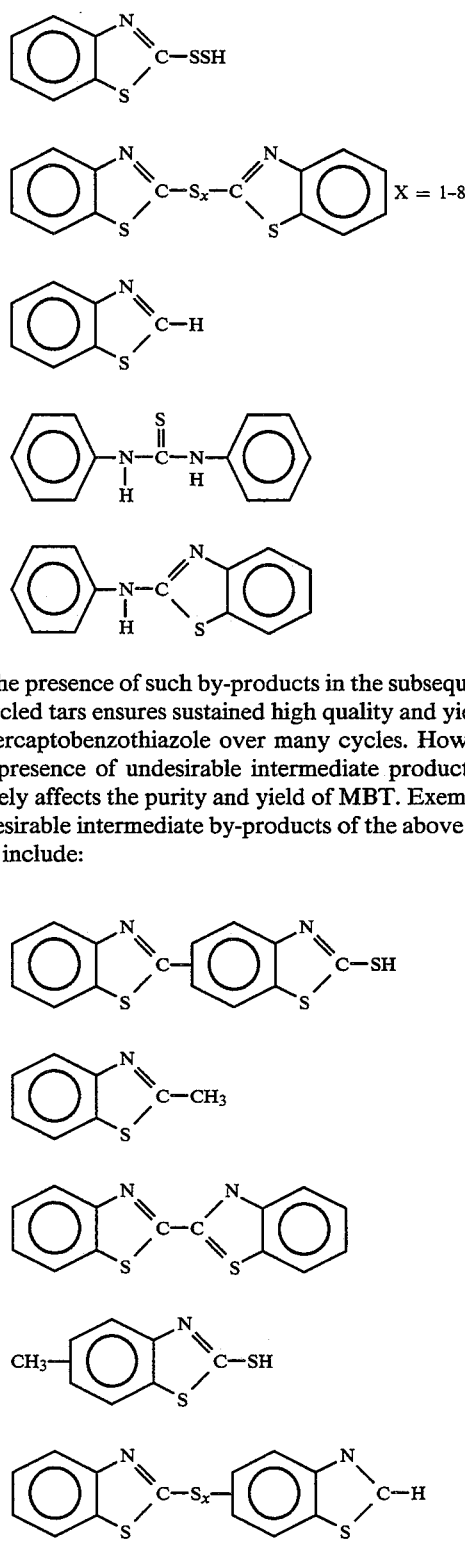

The presence of such by-products in the subsequently recycled tars ensures sustained high quality and yield of 2-mercaptobenzothiazole over many cycles. However, the presence of undesirable intermediate products adversely affects the purity and yield of MBT. Exemplary undesirable intermediate by-products of the above reaction include:

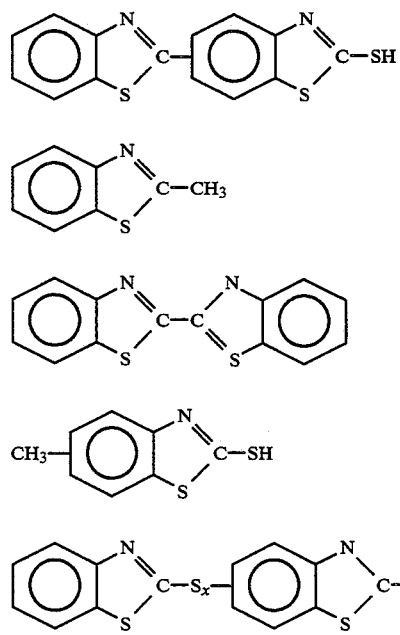

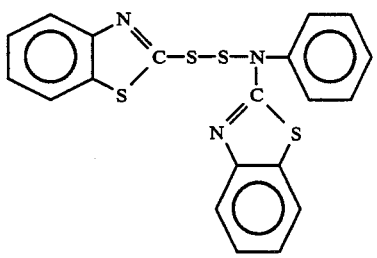

Figure 4:
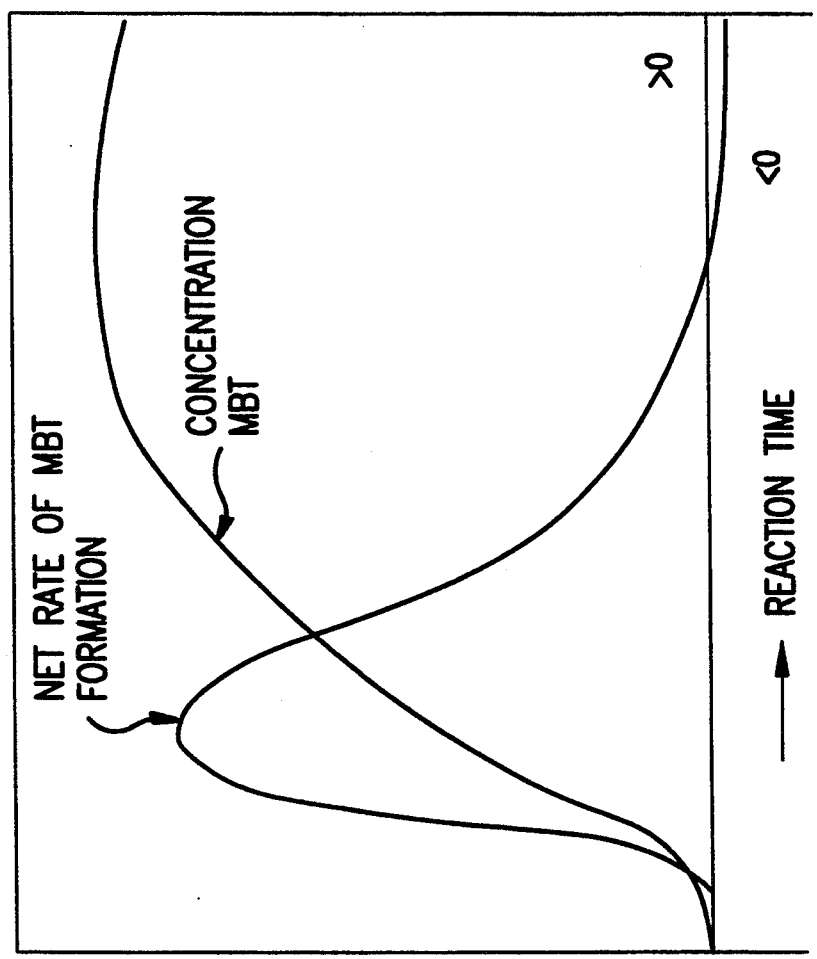
FIG. 4 is a graph comparing concentration of MBT and reaction rate data for an MBT reaction process.

FIG. 4 graphically illustrates the significance of discontinuing a reaction according to the process of the invention before the net rate of MBT formation drops below zero (i.e., the rate of formation of MBT is less than the rate of its decomposition). A reaction which continues beyond this reaction "equilibrium" (when the net rate of MBT formation, curve 2, drops below zero) results in: 1) undesirable amounts of irreversible by-products which cannot subsequently be converted into MBT upon recycling; and 2) a decline in the concentration of MBT (curve 1).

Thus in the process according to the invention, the reaction should be discontinued before the rate of MBT formation is zero or less. This corresponds to the time when irreversible by-products are formed in an undesirable amount.

As a result of the combination of the process features according to the invention, yields of about 98% with a purity of about 99% are achieved. This is the case although according to the law of mass action the amount of hydrogen sulfide remaining in the reaction mixture would have to suppress the formation of MBT.

Preferably, aniline, carbon disulfide and sulfur are added to the recycled intermediates and by-products to obtain a molar ratio of aniline, carbon disulfide and sulfur of 0.8–1.2 : 1–2 : 0.8–1.2, and this reaction mixture is allowed to react under autogenous pressure. Optimum yields and very high purity are obtained if aniline, carbon disulfide and sulfur in a feed molar ratio of 0.9–1.1:1.2–1.7:0.9–1.1 are added to the recycled intermediates and by-products and this reaction mixture is allowed to react under autogenous pressure. The optimum results are obtained in particular if the reaction mixture is reacted at 245°–255° C. and with a reference time of 1.5–2.5 hours under autogenous pressure.

When mixing the reaction mixture with $CS_2$ after termination of the reaction, the temperature and the concentration of $CS_2$ are to be so chosen that a visually clear solution with as high as possible a concentration of MBT is formed. In general, there are 0.7–10 parts by weight of $CS_2$, preferably 0.9 to 3, per 1 part by weight of reaction mixture. For example, after the reaction has been discontinued the temperature of the reaction mixture is 80°–200° C. and that of the $CS_2$ is at most 100°–140° C. The resulting temperature of the solution may preferably be above 100° C. in order to ensure a high MBT concentration. The wash filtrate from the MBT purification step, which substantially consists of $CS_2$ and has a temperature of, for example, 20°–50° C. and in general of about 35° C., can also be used without further purification for preparation of the solution.

It is possible either to add the reaction mixture in a second pressure vessel to the $CS_2$ or to add the $CS_2$ to the reaction mixture. The preferred embodiment is the process according to the invention in which the crude reaction mixture is transferred immediately after the end of the residence time into a pressure vessel into which $CS_2$ has been initially introduced. This procedure enables the intended residence time to be precisely maintained because as a result of the rapid cooling of the reaction mixture, the reaction is terminated immediately. Preferably, the $CS_2$ initially introduced has a temperature of below 100° C., preferably between 30° and 100° C.

In an exemplary process, the reaction mixture may be continuously fed into a tubular reactor, or a sequence of continuous tank reactors, connected in series. The tubular reactor has a means for thermal control, said means maintaining a uniform reaction temperature along a cross-section of the reactor. In addition, the tubular reactor must be of sufficient strength to withstand pressure at the reaction temperature. The pressure is preferably maintained sufficiently high in order to keep the reaction mixture in a one-phase, liquid-state. In the continuous tank reactors, the residence time distribution and mean residence time of the reaction correspond to those of a tubular reactor.

Even after mixing with the carbon disulfide, the crude MBT remains under the autogenous pressure of the hydrogen sulfide evolved during the reaction for formation of MBT. During quenching, the reaction pressure ranges between 10 and 60 barr.

The homogeneous mixture is finally cooled to a temperature of between 20° and 70° C., preferably between 20° and 60° C., more preferably, between 45 and 70° C. Exemplary cooling periods range from between 1.5 an 4.0 hours, preferably 0.8–4.0 hours, the pure MBT being obtained as fine-grained crystals and the unconverted starting compounds and the by-products, and also small amounts of MBT, remaining in the mother liquor. $H_2S$ is removed completely by lowering the pressure only after crystallization.

Preferably, the pressure essentially generated by hydrogen sulfide is adjusted by releasing the pressure such that the pressure remains at least 1.5 MPa (15 bar) after cooling to 150° C. and at least 0.6 MPA (6 bar) after cooling to 100° C.

After cooling of the solution, the precipitated MBT is filtered or centrifuged off from the mother liquor, washed with approximately 1 to 3 times the amount of carbon disulfide and dried under a nitrogen atmosphere or optionally under vacuum in a dryer at 50°–100° C.

The mother liquor obtained after filtration is in the form of a solution containing unconverted aniline and sulfur, the by-products formed, and also small amounts of MBT, in carbon disulfide, and is recycled into the process for the preparation of MBT. This way makes it necessary, depending on the amount of carbon disulfide employed for the purification, to concentrate the mother liquor. Carbon disulfide is distilled off until the amount of carbon disulfide required for the next batch remains. This carbon disulfide and the unconverted starting materials and by-products are then recycled into the reactor, to which, finally, fresh aniline and fresh sulfur are also fed, specifically in amounts such that the proportions of the three reactants are restored to those necessary for the MBT synthesis. In the inventive process, there is no need to analyze the composition of the mother liquor. It does not matter that the respective components are not in their original proportions. The $CS_2$ recovered can be re-used to prepare the solution or for washing.

The filtered mother liquor for recycling may preferably be fractioned (e.g., by extraction, distillation or any other suitable process) to remove undesirable intermediate products which would subsequently decrease the quality of said 2-mercaptobenzothiazole. The resulting fractioned mixture comprises highly active intermediates which may be subsequently recycled.

Figure 2:
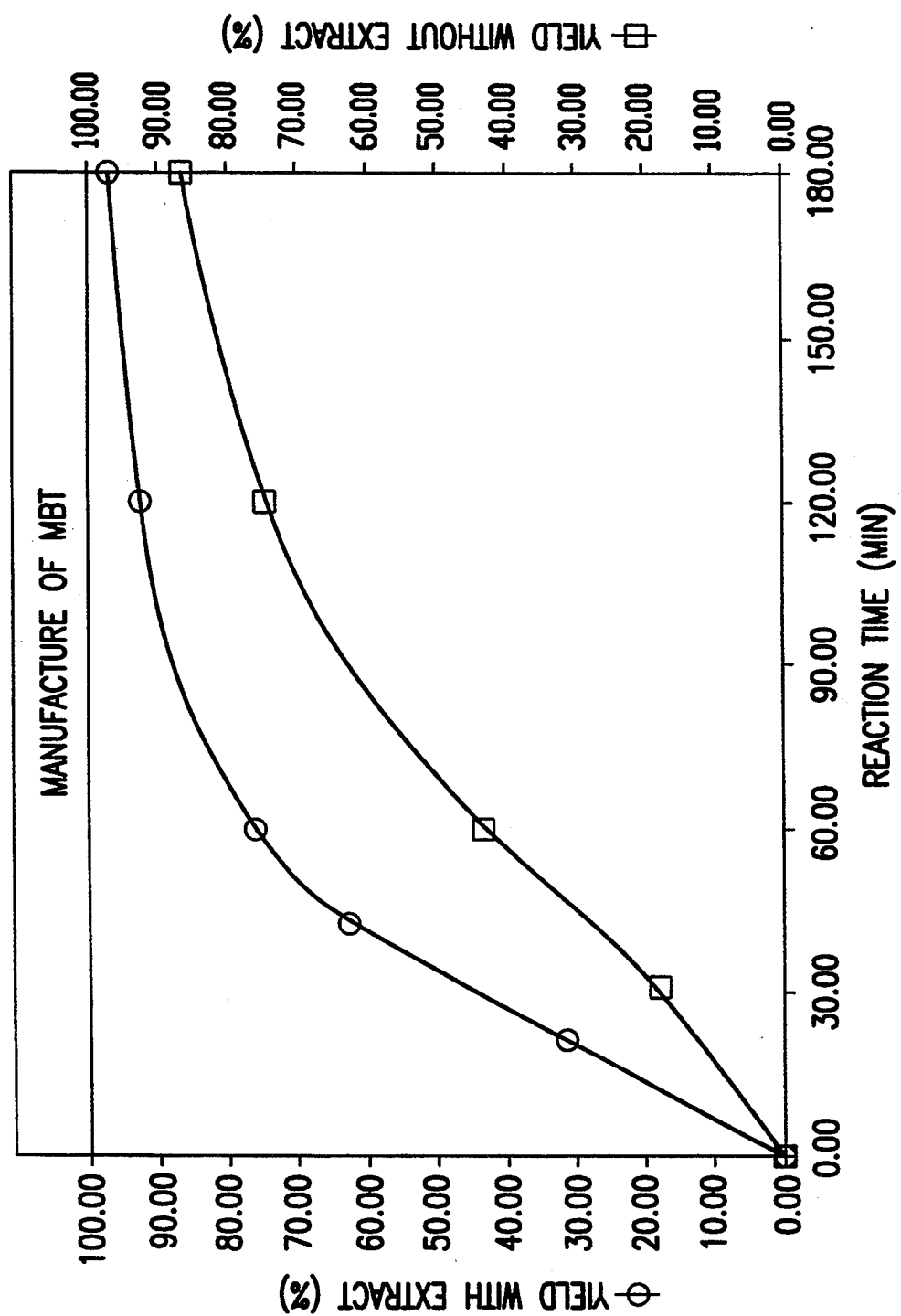
FIG. 2 shows the difference in yields for reactions with and without recycling the mother liquor.

Additionally, the filtered mother liquor may be treated with hydrogen sulfide, or a mixture of hydrogen sulfide and hydrogen under pressure to increase the activity of resulting tars for use in subsequent reaction products. FIG. 2 graphically illustrates the advantages of a process according to the invention which makes use of tars, as compared with a process which does not use recycled tars. After two hours, the yield of 2-mercaptobenzothiazole using tars is 92%, as compared without tars −75%.

It has now been found that the procedure according to the invention leads to an acceleration of the reaction to form MBT (see example 2). An autocatalytic effect can thus be assumed, because the by-products obtained according to the invention apparently accelerate the present reaction for the formation of MBT. The reason for this is that not only the presence of hydrogen sulfide but also the shortened reaction time lead to the constituents of the by-products of the reaction mixture being of a different composition than in the case of the prior art. This also has the advantage that the mother liquor is not loaded with impurities from secondary reactions or decomposition reactions and a large number of recyclings of mother liquor can be carried out. The number of cycles is virtually unlimited if a small portion of the mother liquor is removed from the circulation with each cycle.

Figure 1:
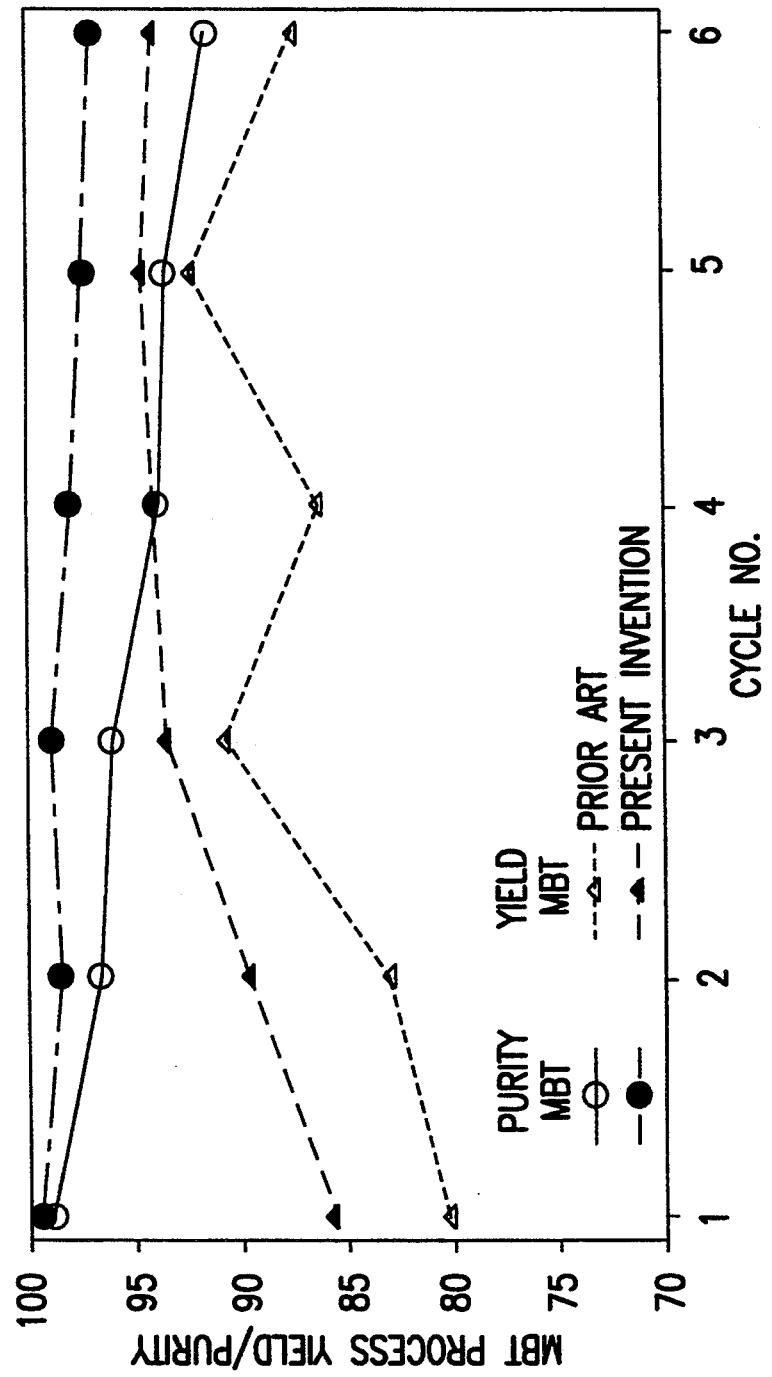
FIG. 1 compares yield and purity of 2-mercaptobenzothiazole for a process disclosed in U.S. Pat. No. 3,031,073 ("prior art") and the process of the present invention.

As illustrated in FIG. 1, the present invention provides for a higher yield and purity of the desired 2-mercaptobenzothiazole, as compared with a conventional process, over six cycles. Both yield and purity using the conventional process are less than those obtained in the present invention. The preparation of MBT in a total yield of about 98% is achieved according to the invention. Such yields and purity according to the present invention are exceptional and unexpectedly high in comparison to conventional processes.

Figure 3:
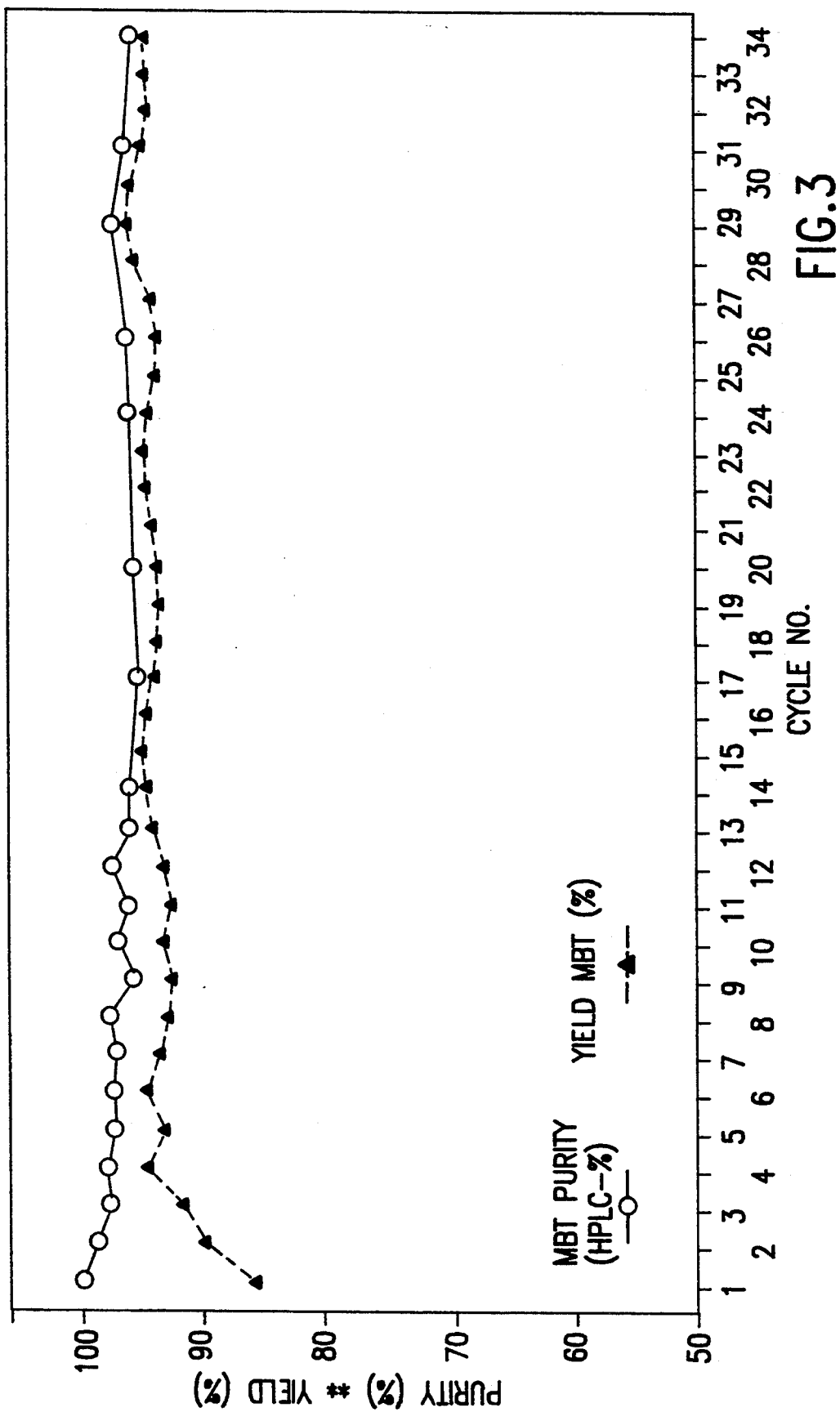
FIG. 3 is a graph representing the yield and purity of MBT obtained in a representative reaction over 34 cycles.

FIG. 3 illustrates purity and yield results from a continuous reaction of 34 cycles. As evidenced by these results, the present invention permits higher yields and purity over a significant number of cycles.

The product purified according to the invention is obtained in the form of fine-grained material which does not dust and is free-flowing, that is to say very easy to handle.

FIG. 4 is a graph representing yield and reaction rate.

The present invention illustrated in more detail by the following examples:

EXAMPLE 1

A 1.3 liter pressure autoclave with a paddle stirrer was charged, in each case, with the following batch (see table):
- 153 g of aniline
- 52.6 g of sulfur, sublimed
- 187.4 g of carbon disulfide (technical grade) mother liquor from the preceding experiment containing Xg of solid residue.

The reactor was closed and heated to 250° C. The residence time was 2 hours, measured from the time when the target temperature was reached.

After termination of the reaction, the mixture was cooled to 180° C. and 600 g of carbon disulfide were pumped into the reactor in the course of 20 minutes. When the addition of $CS_2$ was complete, the reactor was cooled to 28° C. in the course of 2.5 hours. Only then was the pressure lowered and $H_2S$ removed. The reactor was emptied and the suspension separated on a laboratory filter (vacuum filtration). The filter cake was finally rinsed with about 700 g of carbon disulfide and then dried in vacuo at 50° C.

The filtrate was concentrated in a rotary evaporator at 50° C. Both the concentrated mother liquor and the carbon disulfide recovered were re-used for the next batch. The amounts of aniline and sulfur converted to MBT are replaced.

TABLE 1

| Cycle | Recycled by-products (g) | Yield MBT (g) | Purity HPLC % by weight | Purity Titr % by weight | Melting point (°C.) | Space time yield kg/m³h |
|---|---|---|---|---|---|---|
| 1 |  | 159 | 99.7 | 99.4 | 182.7 | 217 |
| 2 | 96.4 | 241.7 | 99.2 | 99.2 | 182.8 | 330 |
| 3 | 125.9 | 281.9 | 98.0 | 98.9 | 182.4 | 383 |
| 4 | 131.2 | 264.0 | 97.7 | 99.0 | 182.3 | 360 |
| 5 | 145.5 | 264.3 | 96.9 | 99.1 | 182.0 | 361 |
| 9 | 188.3 | 271.8 | 97.4 | 98.3 | 181.5 | 371 |
| 13 | 241.1 | 280.5 | 97.0 | 98.9 | 181.1 | 382 |
| 15 | 243.0 | 270.9 | 97.3 | 98.4 | 181.6 | 369 |
| 18 | 239.5 | 265.0 | 97.4 | 98.3 | 180.9 | 362 |

The color of the coarse crystalline MBT ranges from a very pale yellow to a pale beige.

EXAMPLE 2

0.2 mol of aniline, 0.2 mol of sulfur and 0.3 mol of carbon disulfide were introduced into a pressure reactor having a capacity of 100 ml and stirred in said reactor, with the aid of a magnetic stirrer, at 250° C. and under the autogenous hydrogen sulfide pressure generated, for a specific time indicated in Table 2 below. At the end of the residence time, the contents of the reactor were cooled rapidly, the hydrogen sulfide pressure was lowered and the contents of the reactor were taken up in methanol. The methanol solution was then evaporated to dryness. The MBT content of the solid was determined with the aid of HPLC and the total yield of the reaction was calculated from this.

Under otherwise identical conditions, further experiments were carried out in which, in each case, mother liquor containing 25 g of intermediates and by-products, as obtained from the preparation of 2-mercaptobenzothiazole described in Example 1, was mixed into the reaction mixture. The MBT content of the mother liquor was taken into account when calculating the reaction yield.

TABLE 2

| Reaction temperature | Residence time (min) | MBT yield (%) With recycling of mother liquor | MBT yield (%) Without recycling of mother liquor (comparison) |
|---|---|---|---|
| 250° C. | 30 | 48 | 19 |
| 250° C. | 60 | 77 | 43.5 |
| 250° C. | 90 | 87.5 | 64.5 |
| 250° C. | 120 | 93.2 | 74 |
| 250° C. | 180 | 96.3 | 85.6 |

EXAMPLE 3

204.9 g of aniline, 70.5 g of sulfur, 251.3 g of carbon disulfide and 375 g of by-products from an earlier cycle were reacted at 250° for a residence time of 2 hours in a 1 l pressure autoclave. The residence time was taken as the time after the reaction temperature of 250° C. was reached.

The hot melt was transferred to a crystallizer of 2 l capacity, into which 760 g of carbon disulfide at a temperature of 108° C. had been initially introduced. The mixing temperature was 145° C., at which a measurable reaction no longer takes place. The transfer of the hot melt was effected under the full autogenous $H_2S$ pressure. On cooling to room temperature at a rate of 0.8 K./min, the MBT crystallized out, $H_2S$ being gradually removed. The solid MBT was filtered off, rinsed with 400 g of $CS_2$ and dried in vacuo at 50° C.

EXAMPLE 4 (Comparison Example)

The procedure of Example 3 was repeated except that after a residence time of 2 hours at 250° C. the pressure autoclave under the autogenous $H_2S$ pressure of 56 bar was lowered and $H_2S$ was thus removed before the transfer to the crystallizer.

EXAMPLE 5 (Comparison Example)

The procedure of Example 3 was repeated, except that the residence time at the reaction temperature of 250° C. was 5 hours. In this case also the transfer to the crystallizer was made under the full autogenous $H_2S$ pressure.

The product characteristics of the MBT obtained in Examples 3, 4 and 5 are compared in Table 3, from which it is seen that using the process according to the invention, MBT is obtained not only in a high space-time yield but also in high purity.

TABLE 3

|  | Example 3 | Example 4 (comparison) | Example 5 (comparison) |
|---|---|---|---|
| Weight of MBT | 361.6 g | 341.1 g | 348.9 g |
| Appearance | Powder, yellow | Powder, brown | Powder, brown |
| Color (Gardner I) (13% Na-MBT solution) | 12 | 18 | 16 |
| Purity, HPLC | 97.4% by weight | 94.9% by weight | 95.9% by weight |
| Purity, titrimetric | 98.8% by weight | 97.2% by weight | 97.8% by weight |
| Melting point | 180.6° C. | 179.8° C. | 179.7° C. |
| Purity of TLC | 98.9 mol % | 97.5 mol % | 97.8 mol % |

EXAMPLE 6

Aniline, sulfur and $CS_2$, including the by-products from a previous experiment, are measured into a wall-cooled tubular reactor 10 m long and with a length-to-diameter ratio of 2500, in liquid form, in a molar ratio of 1:1:1.3 at a pressure of approximately 150 bar. The residence time is 2 hours at an isothermal reaction temperature of 250° C. The reaction mixture, including all the $H_2S$, is released at the end of the reactor through a throttle valve into a buffer container that keeps the reaction melt with the $H_2S$ at a temperature of approximately 200° C. After the product of two hours' reaction is collected, the contents are suddenly released into a crystallizer to which approximately 250 grams of $CS_2$ at a temperature of 50° C. are added and a mix temperature of approximately 120° C. is obtained. While retaining the entire $H_2S$ amount in the crystallizer, the crystallizer contents are cooled at a linear rate of 0.8° C./minute. Crystallization occurs in the temperature range from 75° to 90° C. After crystallization occurs, the $H_2S$ is released from the crystallizer, while cooling is performed at the same rate until a final temperature of 25° C. is reached.

The MBT that has crystallized out is filtered off and washed with a small amount of $CS_2$ and then dried. The mother liquor filtrate is concentrated at 50° C. under vacuum and returned to the reactor, together with fresh reactants: aniline, sulfur, and $CS_2$.

After 25 such cycles, MBT is obtained, with an average purity of 98.5% (HPLC) as well as an average yield of 99.45% based on the aniline added.

What is claimed is:

1. A process for the preparation of 2-mercaptobenzothiazole, comprising:

reacting aniline, sulfur and carbon disulfide under autogenous pressure in a reactor, without releasing hydrogen sulfide, for a reactor residence time and at a reaction temperature of 220–280° C. to form a crude reaction product, said residence time ranging from at least one hour to a time before the 2-mercaptobenzothiazole product thus-formed decomposes in an undesirable manner, resulting in irreversible by-products;

discontinuing the reaction when the residence time has elapsed, without releasing hydrogen sulfide produced;

quenching said hot crude reaction product, without removing hydrogen sulfide present in the crude reaction product, by mixing the crude reaction product with carbon disulfide, said carbon disulfide being at a temperature sufficient to obtain a homogeneous quenched mixture;

cooling said homogeneous quenched mixture to a temperature sufficient to crystallize said 2-mercaptobenzothiazole without removing hydrogen sulfide present in the cooled reaction product and thereby maintaining a maximum hydrogen sulfide pressure until after crystallizing a substantial amount of said 2-mercaptobenzothiazole;

further cooling the mixture;

removing hydrogen sulfide from said reactor; and isolating the crystallized 2-mercaptobenzothiazole from a mother liquor.

2. The process according to claim 1, wherein during the cooling, an amount of hydrogen sulfide not greater than one half the maximum hydrogen sulfide generated is released.

3. The process according to claim 1, wherein during further cooling, hydrogen sulfide is completely released.

4. The process according to claim 2, wherein during further cooling, hydrogen sulfide is completely released.

5. The process according to claim 1, further comprising:

separating a part of the carbon disulfide from said mother liquor; and recycling at least part of the mother liquor into the reactor after mixing with an amount of aniline and sulfur.

6. The process according to claim 5, wherein the mother liquor is recycled with an amount of carbon disulfide.

7. The process according to claim 5, further comprising:
recycling said mother liquor more than once without analyzing its composition; and
feeding unvarying amounts of aniline, carbon disulfide and sulfur reactants in each corresponding recycle, wherein each corresponding recycle uses a residence time in the reactor shorter than an initial residence time, without recycling.

8. The process according to claim 2, further comprising:
separating a part of the carbon disulfide from said mother liquor; and
recycling at least part of the mother liquor into the reactor after mixing with an amount of aniline and sulfur.

9. The process according to claim 1, wherein the pressure in the reactor during further cooling of the cooled reaction product, upon crystallization, ranges from between about 10 to about 60 bar.

10. The process according to claim 1, wherein the carbon disulfide temperature ranges from about 30 to about 100° C.

11. The process according to claim 1, wherein said quenching occurs after all of the aniline has been reacted.

12. The process according to claim 1, wherein the further cooling temperature ranges from between about 20° and about 70° C.

13. The process according to claim 1, wherein the further cooling temperature ranges from between about 45° and about 70° C.

14. The process according to claim 1, wherein a cooling time of the quenched reaction product ranges from about 0.8 to 4.0 hours.

15. The process according to claim 6, wherein said aniline, carbon disulfide and sulfur are added to the mother liquor to obtain a molar ratio of 0.8–1.2: 1–2:0-.8–1.2, respectively, as a recycle feed.

16. The process according to claim 15, wherein said molar ratio is 0.9–1.1:1.2–1.7:0.9–1.1.

17. The process according to claim 1, wherein the crude reaction product is mixed with said carbon disulfide in a weight ratio of 1:0.7 to 10.

18. The process according to claim 17, wherein said weight ratio is 1:0.9 to 3.

19. The process according to claim 1, wherein said reaction temperature is 245°–255° C. and said residence time is 1.5–2.5 hours.

20. The process according to claim 2, wherein the total pressure due to the presence of hydrogen sulfide and carbon disulfide is controlled to maintain: 1) at least 1.5 MPa, after cooling to about 150° C.; and 2) at least 0.6 MPa, after cooling to about 100° C.

21. The process according to claim 5, further comprising fractioning all or a part of the mother liquor to remove undesirable, irreversible by-products which would subsequently decrease the quality of said 2-mercaptobenzothiazole.

22. The process according to claim 21, wherein said fractioning is carried out by extraction.

23. The process according to claim 21, wherein said fractioning is carried out by distillation.

24. The process according to claim 21, wherein the fractioned, mother liquor comprises highly active intermediates, which may be recycled in subsequent reaction cycles.

25. The process according to claim 5, comprising treating the at least part of the mother liquor with hydrogen sulfide under pressure to increase the activity of said mother liquor for use in subsequent reaction cycles.

26. The process according to claim 5, comprising treating the at least part of the mother liquor with a mixture comprising hydrogen sulfide and hydrogen under pressure to increase the activity of said mother liquor for use in subsequent reaction cycles.

27. The process according to claim 1, wherein the reaction mixture is continuously fed into a tubular reactor, said reactor having a thermal control means for maintaining a uniform reaction temperature along a cross-section of the reactor and said tubular reactor having sufficient mechanical strength to withstand the pressure at the reaction temperature.

28. The process according to claim 27, wherein the reactor pressure is maintained sufficiently high to keep the reaction mixture in a single, liquid phase.

29. The process according to claim 1, wherein the reaction is carried out in a sequence of continuous tank reactors connected in series.

30. The process according to claim 1, wherein said crystallized 2-mercaptobenzothiazole has a melting point of at least 180° C.

31. A process for the preparation of 2mercaptobenzothiazole, comprising:
reacting aniline, sulfur and carbon disulfide under autogenous pressure in a reactor, without releasing hydrogen sulfide, for a reactor residence time and at a reaction temperature of 220°–280° C. to form a crude reaction product, said residence time ranging from at least one hour to a time before the 2-mercaptobenzothiazole product thus-formed decomposes in an undesirable manner, resulting in irreversible by-products;
discontinuing the reaction when the residence time has elapsed, without releasing hydrogen sulfide produced;
quenching said hot crude reaction product, without removing hydrogen sulfide present in the crude reaction product, by mixing the crude reaction product with carbon disulfide, said carbon disulfide being at temperature sufficient to obtain a completely homogeneous quenched mixture;
cooling said-homogeneous quenched mixture to a temperature sufficient to crystallize said 2-mercaptobenzo-thiazole without removing hydrogen sulfide present in the cooled reaction product and thereby maintaining a maximum hydrogen sulfide pressure until after crystallizing a substantial amount of said 2-mercaptobenzothiazole;
further cooling the mixture;
removing hydrogen sulfide from said reactor; and
isolating the crystallized 2-mercaptobenzothiazole from a mother liquor.

32. The process according to claim 1, wherein said homogeneous quenched mixture is a visually clear solution.

33. The process according to claim 1, wherein said homogeneous quenched mixture is at a temperature of at least about 80° C.

34. The process according to claim 33, wherein said temperature is between about 80° C. and about 200° C.

* * * * *